US006277583B1

(12) United States Patent
Krantz et al.

(10) Patent No.: US 6,277,583 B1
(45) Date of Patent: *Aug. 21, 2001

(54) AFFINITY LABELING LIBRARIES AND APPLICATIONS THEREOF

(75) Inventors: Alexander Krantz, Menlo Park; Arthur M. Hanel, San Francisco; Wolin Huang, Foster City, all of CA (US)

(73) Assignee: Conjuchem, Inc., Montreal (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/598,054

(22) Filed: Feb. 7, 1996

(51) Int. Cl.$^7$ .................. G01N 33/53; G01N 33/566; A61K 38/00
(52) U.S. Cl. ............... 435/7.1; 530/300; 530/344; 530/380; 436/501; 436/536; 435/DIG. 1; 435/DIG. 2; 435/DIG. 14; 435/DIG. 15; 435/DIG. 34
(58) Field of Search .................. 530/380, 300, 530/344; 436/536, 501; 435/7.1, DIG. 1, DIG. 2, DIG. 14, DIG. 15, DIG. 34

(56) References Cited

U.S. PATENT DOCUMENTS

| | | | |
|---|---|---|---|
| 4,767,710 | * 8/1988 | Bigbee et al. | 435/240.27 |
| 4,971,792 | 11/1990 | Steplewski et al. | 424/1.49 |
| 5,182,366 | 1/1993 | Huebner et al. | 530/334 |
| 5,270,170 | 12/1993 | Schatz et al. | 435/7.37 |
| 5,510,240 | * 4/1996 | Lam et al. | 435/7.1 |
| 5,571,681 | 11/1996 | Janda . | |

FOREIGN PATENT DOCUMENTS

| | | |
|---|---|---|
| 0639584 | 2/1995 | (EP) . |
| 0742438 | 11/1996 | (EP) . |
| WO92/09300 | 6/1992 | (WO) . |
| WO93/20242 | 10/1993 | (WO) . |
| WO94/06291 | 3/1994 | (WO) . |
| WO94/06451 | 3/1994 | (WO) . |
| WO 94/26787 | * 11/1994 | (WO) . |
| 95/34575 | 12/1995 | (WO) . |
| 96/24061 | 8/1996 | (WO) . |

OTHER PUBLICATIONS

Ghose, T., et al. "Antibody–Linked Cytotoxic Agents in the Treatment of Cancer: Current Status and Future Prospects", *J. Nat'l. Cancer Inst.*, 61(3):657–676 (1978).

Lambert, J.M., et al. "Purified Immunotoxins That Are Reactive with Human Lymphoid Cells", *Journal of Biological Chemistry*, 260(22):12035–12041 (1985).

Gillies, S.D., et al. "Antigen binding and biological activities of engineered mutant chimeric antibodies with human tumor specificities", *Hum. Antibod. Hybridomas*, 1(1):47–54 (1990).

Tao, M.H., et al., "Role of Carbohydrate in the Structure of Effector Functions Mediated by the Human IgG Constant Region", *Journal of Immunology*, 143(8):2595–2601 (1989).

Coller, B.S., et al., "Thromboerythrocytes In Vitro Studies of a Potential Autologous, Semi–artificial Alternative to Platelet Transfusions", *J. Clin. Invest.*, 89:546–555 (1992).

Gordon, E.M., et al., "Applications of Combinatorial Technologies to Drug Discovery. 2. Combinatorial Organic Synthesis, Library Screening Strategies, and Future Directions", *Journal of Medicinal Chemistry*, 37(10):1385–1401(1994).

\* cited by examiner

*Primary Examiner*—Padmashri Ponnaluri
(74) *Attorney, Agent, or Firm*—Morrison & Foerster LLP (57) ABSTRACT

Novel methods and compositions are provided for preferentially bonding an oligomeric molecule to a macromolecular target where the target is a member of a complex mixture and/or there is preferential bonding at one of a plurality of available bonding sites of the macromolecular target. The methods represent a complete system for both producing and identifying affinity label molecules from a combinatorial library which preferentially bind to a marcomolecular target or target site and preferentially binding those affinity labels to a macromolecule of interest either ex vivo or in vivo. Macromolecular targets include a variety of cellular- and non-cellular-associated proteins.

9 Claims, 2 Drawing Sheets

AFFINITY LABELING LIBRARIES AND APPLICATIONS THEREOF

Introduction

1. Technical Field

The field of this invention is the specific covalent affinity labeling of target macromolecules, affinity labeling libraries and various applications thereof.

2. BACKGROUND

It is frequently desirable to have the ability to covalently link a particular compound of interest to a specific target, e.g. one of a mixture of components or a site on a macromolecule. For example, covalent linkage of a compound to a specific target site on a catalytic enzyme can result in permanent inhibition of the catalytic activity of that enzyme.

Furthermore, covalent linkage of a compound to a specific target site on a biological receptor can result in either agonism or antagonism at that receptor site. Moreover, covalent linkage of a biologically active compound to a specific target macromolecule present in the human vasculature can result in an effective increase in the half-life of that biologically active molecule. Having the ability to specifically and covalently link a compound of interest to a macromolecular target or target site, therefore, can have profound implications for drug design and pharmaceutical therapy in humans.

Except for molecules that exhibit very high binding affinities, non-covalent interactions between two molecules are generally in equilibrium, where a substantial proportion of the molecules remain separated. Therefore, if one wishes to have stable interactions between a molecule and a target site, one usually resorts to covalent bonding.

Non-covalent interactions between two complementary biological molecules, however, are extremely well known in the art. For example, a double-stranded nucleic acid may be constructed from non-covalent interactions between two complementary single-stranded nucleic acids. The two single-stranded nucleic acids possess a specific affinity for one another because of the complementarity of their respective sequences. In addition, a number of biological proteins specifically and non-covalently interact with complementary sites on other macromolecules. These specific non-covalent interactions include such things as receptor/protein interactions and immunoglobulin/antigen interactions.

Both non-covalent and covalent interactions provide alternative means for attaching labels to macromolecular target sites. The hallmark of an affinity label molecule, however, is that it labels a macromolecular target by using both of the above described types of molecular interaction. For example, an affinity label not only possesses a certain degree of specific complementarity with a target macromolecule, but it also forms a stable covalent bond with that target macromolecule. As a result, affinity labels can selectively attach to a macromolecular target or target site in a complex mixture. Affinity labels also generally exhibit a greater degree of preferential binding to their target macromolecule than do other molecules bearing a chemically reactive group but which lack specific complementarity with the target.

Affinity labels which have both a specific complementarity to a macromolecular target and the ability to covalently bind to that target are presently known in the art and have previously been constructed by attaching potentially reactive electrophilic groups to the binding determinants of an enzyme substrate or a ligand for a specific biological receptor. (Methods of Enzymology, Vol. XL VI, 1977, eds., Jakoby, W. B. and Wilchek, M., Academic Press, New York). For example, affinity labeling of enzymes has proven to be successful because enzymes often use a wide assortment of nucleophilic side chains to catalyze their reactions. This provides the opportunity to attach potentially reactive electrophilic groups to enzyme substrate analogs so that binding of those substrate analogs by the enzyme brings those potentially reactive electrophilic groups into close spatial proximity to the nucleophilic side chains of the enzyme. Because the potentially reactive electrophilic groups of the substrate analog are brought into close spatial proximity to the nucleophilic side chains of the enzyme, covalent bonds between these reactive groups may readily form. Thus, enzyme substrate analogs possessing potentially reactive electrophilic groups have proven to be prime candidates for the affinity labeling of enzymes.

Affinity labeling of biological receptors and other non-catalytic proteins, however, has proven to be much less successful, but not necessarily because of difficulties related to identifying a tight binding complementary group. For example, medicinal chemists have been able to produce numerous antagonist molecules which exhibit high specific affinities for receptor targets. However, since biological receptors are not catalytic, it is difficult to know how potentially reactive groups on the receptor molecule and on the affinity label are spatially situated relative to one another without specific structural information. As such, forming covalent bonds between affinity label molecules and non-catalytic proteins has proven to be rather difficult.

Thus, one of the difficulties encountered in the affinity labeling of macromolecular targets is that it is often necessary to possess structural information about the macromolecular target and the location of its potentially reactive sites. A general approach for affinity labeling of macromolecules, therefore, regardless of whether those macromolecules possess catalytic activity and without possessing structural information about those macromolecules, would be invaluable because it would have numerous applications which arise from the ability to specifically link a compound of interest to a macromolecular target or target site in a complex mixture.

Having the ability to affinity label macromolecular targets or specific target sites without requiring that the target be catalytic or without possessing detailed structural information about the target gives rise to numerous beneficial applications. These numerous applications include new opportunities for enzyme inhibition, antagonism and agonism of biological receptors, attaching biologically active compounds to specific target sites in vitro and/or in vivo, e.g., for the purpose of increasing the half-life of those biologically active compounds, labeling macromolecules for premature destruction, directing biologically active compounds to specific sites in vivo and exploiting numerous in vivo sites that have been hitherto difficult to target, including tumorigenic sites. These many applications have profound implications for drug design and discovery, including the generation of specific linkages to specific sites on various living cells and tissues for therapeutic and prophylactic purposes. There is, therefore, substantial interest in providing for improved methods of specifically affinity labeling various macromolecular targets and target sites of interest.

SUMMARY OF THE INVENTION

Novel methods for preferentially producing target protein conjugates between oligomeric affinity label molecules and target proteins are provided. These methods represent a complete system for both producing and identifying affinity label molecules which preferentially bind to a macromolecular target or target site and conjugating those preferentially binding affinity label molecules to a target macromolecule, usually in a complex mixture of macromolecules. The methods comprise combining a mixture of proteins comprising the target protein with an affinity label conjugate comprising an oligomer and a biologically active compound wherein the affinity label conjugate has an activated functional group capable of covalently bonding to a functionality on the target protein. The affinity label conjugate is produced by preparing an oligomeric combinatorial library comprising an activatable functional group and activating the functional group of the members of the combinatorial library. The activated affinity label conjugate members of the combinatorial library are combined with the target protein, selecting one or more members of the combinatorial library which preferentially bind to the target protein. The preferentially binding affinity labels may then be screened further with a mixture of proteins to determine the affinity labels which provide substantial preference for the target protein as compared to the other components in the mixture. Thereafter, the affinity label is covalently joined to a biologically active compound for preferentially bonding the biologically active compound to the macromolecular target protein. Target proteins include a variety of cellular- and non-cellular-associated molecules. Methods for producing and identifying affinity label molecules which preferentially bind to a macromolecular target or target site are also provided.

Once an affinity label or labels that interact with and covalently bond to a macromolecular target or target site are identified from a combinatorial library, methods for enhancing the specificity of labeling of the macromolecular target by those affinity labels are also provided. Such methods comprise identifying affinity label molecules which preferentially bind to a target macromolecule and subsequently lowering the overall reactivity of the activating group coupled to those affinity label molecules.

Site-specific affinity labels may be identified by contacting a macromolecular target of interest with a combinatorial affinity labeling library and identifying the adducts formed to select affinity labels which bond preferentially to a macromolecular target in a mixture, to a single specific site or limited number of sites on the macromolecular target. This method provides a means for directing affinity labels to important site(s) on a macromolecular target either in vivo or in vitro, thereby having significant implications on drug design and development. For example, site-specific affinity labels may be used for such applications as labeling macromolecular targets for modifying that target or to be used for extending the lifetime of a compound of interest, and/or for interfering with the binding of a biological molecule to its respective biological receptor, particularly, allosterically.

DESCRIPTION OF THE SPECIFIC EMBODIMENTS

Methods and compositions are provided for producing oligomeric affinity label molecules and preferentially covalently bonding those oligomeric affinity label molecules to a macromolecular target, where the target is a member of a complex mixture, i.e., such as serum, blood, cerebral spinal fluid, etc., and/or there is preferential bonding at one or a limited number of a plurality of bonding sites on the macromolecular target. The methods described herein represent a complete system for both producing and identifying affinity label molecules from a combinatorial library which preferentially bind to a macromolecular target or target site and preferentially binding those affinity labels to a macromolecule of interest either ex vivo or in vivo.

The methods comprise at least the following steps: preparing a combinatorial oligomeric affinity labeling library, where the members of the library have a functional group which is available for activation;

activating the functional group for covalently reacting with a functionality present on the macromolecular target; combining one or a mixture of members of the combinatorial library with a composition comprising the macromolecular target under conditions where reaction can occur between the activated functional group of an affinity label molecule and a functionality present on the macromolecular target; and determining whether reaction has occurred preferentially between one or more members of the combinatorial library and the macromolecular target.

To further enhance specificity, the oligomers showing preferential binding are used to produce a second mixture where the oligomers are activated to provide a product which reacts more slowly than the previous oligomers with the macromolecular target functionality. In this way, one can further differentiate the binding affinity by selecting one or more oligomers which provide higher levels of bonding to the macromolecular target.

The affinity label molecules of this invention will be oligomeric and have an available functional group for activation. Once activated, affinity label molecules have the ability to specifically interact with and covalently bond to a macromolecular target or target site of interest in a complex mixture. By specifically interacting with and covalently bonding to a macromolecular target or target site is meant that the affinity label will exhibit some preferential binding to the macromolecular target as against other components in the environment in which the affinity label molecule and the macromolecular target will be combined. The preference will normally be at least about 1.5, preferably at least about 2 times, random binding in the absence of the oligomer.

The oligomeric affinity label may be an oligopeptide, oligonucleotide, oligosaccharide, combinations thereof, or the like. Affinity labels will be characterized by being able to be readily synthesized as a combinatorial library, so that the synthetic chemistry is substantially repetitive with the addition of each monomer unit to the growing oligomer. Also, methods will be available for analyzing the composition and/or sequence of the affinity label oligomer.

Generally, the number of monomeric units in each oligomeric affinity label will be from 4 to 12, more usually from 4 to 8 and preferably from 5 to 8. The monomer units comprising the oligomeric affinity label may be naturally occurring or synthetic, generally being from about 2 to 30 carbon atoms, usually from about 2 to 18 carbon atoms and preferably from about 2 to 12 carbon atoms.

If the affinity label is an oligopeptide, the amino acid monomers may be naturally occurring or synthetic.

Conveniently, the naturally occurring L-α-amino acids will be used, although the D-enantiomers may also be employed.

While the amino acid monomers of the oligomer may be any one of the 20 naturally occurring amino acids in either the L- or D-configuration, the amino acids employed will preferentially be free of reactive functionalities, particularly reactive functionalities which would react with the activated functional group. Therefore, the amino acids which are used will usually be free of reactive amino, guanidino and carboxy groups, frequently being free of hydroxy and thiol groups. Of particular interest are the naturally occurring amino acids having hydrocarbon side chains including alanine (A), glycine (G), proline (P), valine (V), phenylalanine (F), isoleucine (I) and leucine (L) or uncharged polar amino acids like methionine (M). Other amino acids which may find use include other aromatic amino acids, such as histidine (H), tryptophan (W), and tyrosine (Y).

The amino acid monomers of the oligomeric affinity label may also be synthetic. Thus, any unnatural or substituted amino acids of from 4 to 30, usually from 4 to 20, carbon atoms may be employed. Of particular interest are the synthetic amino acids β-alanine and γ-aminobutyrate or functional group protected amino acids such as O-methyl-substituted threonine (T), serine (S), tyrosine (Y), or the like.

Amino acids which find use may have the carboxyl group at a site other than the terminal carbon atom, may have the amino group at a site other than the α-position or may be substituted with groups other than oxy, thio, carboxy, amino or guanidino, e.g. cyano, nitro, halo, particularly fluorine, oxo, inorganic acyl groups, etc.

Synthetic amino acids may also be monosubstituted on nitrogen as in peptoids, which are oligomers of N-substituted glycine residues. N-substituted amino acids which find use will have an N-substituent of from about 1 to 8, usually 1 to 6 carbon atoms, which may be aliphatic, alicyclic, aromatic or heterocyclic, usually having not more than about 3 heteroatoms, which may include amino, either tertiary or quaternary, oxy, thio, and the like.

Oligopeptides may be constructed by employing standard Merrifield solid phase synthetic methods, manually or by using an automated peptide synthesizer, standard protection chemistry (e.g., t-Boc or Fmoc chemistry) and resins (e.g., 4-methyl benzhydryl amine Rink Amide resin). Successive rounds of deprotection of the terminal amino group and coupling of amino acid monomers, followed by deprotection and cleavage of peptides from resins results in the synthesis of oligopeptides of the desired sequence and length. A functional group on the oligopeptide may then be activated and the activated oligomer either liberated from the solid support. Alternatively, the oligopeptide may be liberated or assayed on from the support and the available functionality subsequently activated. Additionally, liquid phase peptide synthesis is well known in the art and may also be employed.

If the amino acid monomers employed are N-substituted glycine residues, monomers may incorporate t-butyl-based side chain and 9-fluorenylmethoxycarbonyl α-amine protection. (See, for example, Gordon et al., J. of Medicinal Chemistry (1994) 37, 1387–1385, and references cited therein). Controlled oligomerization of the N-substituted monomers may be performed manually and/or robotically with in situ activation by either benzotriazol-1-yloxytris (pyrrolidino)-phosphonium hexafluorophosphate or bromotris (pyrrolidino) phosphonium hexafluorophosphate. Additional steps may follow standard automated peptide synthesis protocols using α-(9-fluorenylmethoxycarbonyl) amino acids.

If the affinity label is an oligonucleotide, either naturally occurring or synthetic nucleotide monomers may be employed.

Particularly, for synthetic nucleotides, the phosphate or sugar groups may be modified where phosphate may be substituted by having the oxygen atoms replaced with sulfur or nitrogen, the phosphate group may be replaced with sulfonate, amide etc., the ribose or deoxyribose may be replaced with 5 to 6 carbon atom sugars such as arabinose, fructose, glucose, or the like, and the purines and pyrimidines may be modified by substitution on nitrogen, with alkyl or acyl, may employ different ring structures, may have nitrogen replaced by oxygen, or vice versa, and the like.

If the affinity label is an oligosaccharide, the oligosaccharide will usually have from 4 to 6 monomeric units which may be linear or branched, comprised of sugars of from 5 to 8 carbon atoms. Various modifications of known oligosaccharides may be employed, particularly where one is interested in binding to lectins or adhesion molecules.

Combinatorial affinity labeling libraries may be prepared in accordance with conventional ways for producing combinatorial libraries, particularly using a solid support and adding the monomeric components in a stepwise manner. See, for example, Gordon et al. (1994), supra, U.S. Pat. Nos. 5,182,366 and 5,270,170 and WO92/09300; WO93/20242; WO94/06451; and WO94/06291. Preferably, the synthetic chemistry is substantially repetitive with the addition of each monomer unit to the growing oligomer.

Combinatorial libraries of oligomeric affinity labels are usually constructed by synthesizing a substantial proportion of the different permutations possible for an affinity label of the desired size and length based on the number of selected monomers. Usually, combinatorial affinity labeling libraries are synthesized in a stepwise fashion where one of a number of different monomer types (including naturally occurring or synthetic amino acids, nucleotides or saccharides) is coupled to another one of a number of different monomers of the same type, thereby generating multiple independent and distinct pools, each comprising numerous different dimers. This process is then repeated in an iterative manner to construct combinatorial libraries of the desired complexity containing oligomeric affinity labels of the desired size and length. Synthetic methods such as pool splitting or the like may be employed to allow the identity of one or more of the monomer units of the oligomers to be known. Combinatorial affinity labeling libraries will have at least about 100 members, usually at least about 500 members, preferably at least about 1,000 members and frequently 10,000 or more members.

Once synthesized, an available functional group on the members of the affinity labeling library is then activated so as to be able to covalently react in the environment in which the reaction is to occur with a functionality present on a macromolecular target. For the most part, the reaction will occur in an aqueous environment, which may be a complex environment such as blood or plasma.

While any activated functional group which specifically reacts with the available functionality of the macromolecular target may be used, for the most part, the functionality on the macromolecular target will be amino, and the activated functional group of the affinity label will be carboxy, phosphoryl, or other convenient acyl group, either as an ester or a mixed anhydride, or an imidate. The activated functional group may be present at any position on the members of the combinatorial library, but will usually be proximal to one or the other terminus. Conveniently, a member of the affinity label oligomer may carry the activated functional group, such as aspartate, glutamate or homoglutamate. By having one of these amino acids in the chain of every oligomer, there will be present an available functional group for activation in each oligomer.

Useful libraries can be prepared where one specifies the first 2 to 3 amino acids of the oligopeptides, followed by randomization of the remaining amino acids, usually from 2 to 3 amino acids. Thus, one can prepare 6, conveniently 8 to 12, or more di- or tripeptides, of known composition bound to a support and extend the oligopeptide by adding mixtures of amino acids to each successive terminal amino acid, so that one may have 6 or more, usually about 8 to 12 and not more than about 14 amino acids at each successive position. As exemplified in the experimental section, the oligopeptide is prepared with three known amino acids, the first amino acid providing the functional group for activation, followed by two additional amino acids, where mixtures of ten amino acids are employed. By employing ten different combinations of the second and third amino acids, one can produce 10,000 different oligopeptides.

The monomer with the activated functional group may be added at the same position of every oligomer or may be at different positions of the oligomer to provide greater diversity to the library. Alternatively, where the oligomer is bound to a surface through a linking group, upon cleavage of the linking group, there can be an available functionality for activation or modification to provide the carboxyl functionality. For example, where an oxy group results, the oxy group may be reacted with an α-halocarboxylic acid, e.g., α-chloroacetic acid, to provide the carboxyl functionality. Other functionalities and reactions may be employed depending upon the nature of the linking group and the desired nature of the library.

For activation of the carboxyl group, one may use a wide variety of anhydride or ester leaving groups, where the leaving group may have oxygen or sulfur bonded to carbonyl. Groups which may be employed may vary depending on whether one is screening the library, using the member of the combinatorial library for reaction or varying the reactivity of the activated functional group to vary the selectivity of the affinity label. In some instances, particularly screening, one may select a leaving group which may be detected, directly or indirectly, spectrophotometrically. In other instances where one is interested in sing the product in vivo, one may select the group to be physiologically acceptable. Compounds which may be used to activate the carboxyl functional group include carbodiimides, phenols such as p-nitrophenol, thiophenols such as thiophenol, benzyl alcohols, N-hydroxy imides such as N-hydroxy succinimides, phosphates, such as o-phenylphosphate, coumarins, such as s5-trifluoromethyl-7-aminocoumarin, 2-hydroxyethyl benzoate, etc.

When other than the functional group of a monomeric unit of the oligomer, the oligomeric affinity label and the activated functional group may be joined by either a bond or a linker entity having a chain of from about 1 to 20, usually 1 to 12 and more usually 1 to 8 carbon atoms. A linker entity may vary in size and length, thereby providing a means for displacement of the affinity label from the activated functional group when the macromolecule is in solution. Conveniently, the linker entity may be the group used to attach the first monomer to a solid support for synthesis of the oligomeric affinity label. If so, cleavage of the completely synthesized oligomer from the solid support makes available a functional group for activation. A large variety of linker entities have been found to be satisfactory for linking the first monomer of the affinity label to a support and these will frequently be useful for the purposes of the subject invention.

Once functional groups on the members of the combinatorial library are activated, the activated members are then combined, either individually or in limited groups, with the macromolecular target, whereby different proportions of each of the library members will become covalently bound to the target molecule and the binding affinity of the various members to the macromolecular target is determined. The macromolecular target will usually be a protein so that reactive functionalities available for covalent bond formation with the activated functional group of the oligomeric affinity label will be usually amino and thiol groups. Preferably, for the most part, the macromolecular reactive functionality of choice for covalent bond formation will be amino groups.

The macromolecular targets will be proteins, either individually, as aggregates with the same or different proteins or as surface membrane proteins. Particular proteins, either individually or as part of cells, include the surface membrane proteins of erythrocytes, particularly glycophorin A and Band 3, and C, T or B cell surface proteins, such as CD3, B7, p28, CTLA-4, CD34, Thyl, CD4, CD8, LFA1, CD5, sIgE, sIgM, platelet proteins, such as IIb/IIIA, leukocyte surface membrane proteins, serum albumin, immunoglobulins, particularly IgG and IgM, apolipoproteins, such as LDL, HDL and VLDL, and proteins associated with chylomicrons, endothelial cell surface proteins, such as integrins, adhesion proteins, etc.

Cells for targeting include platelets, erythrocytes, endothelial cells, T cells or subsets thereof, B cells or subsets thereof, other leukocytes, such as macrophages, monocytes, neutrophils, basophils, NK cells, eosinophils, stem cells, such as hematopoietic stem cells, tumorous or malignant cells, infected cells, such as virally infected, e.g., retroviruses such as HIV, DNA viruses, such as hepatitis B or C virus, etc. The cells may be fixed or mobile.

A number of proteins of interest have numerous reactive functionalities for reaction ex vivo or in vivo. For example, human serum albumin, glycophorins, thrombin, adenylate kinase, plasminogen, β-lactamase, ACE, glutathione transferase, HMG CoA reductase, gastric lipase, and lecithin:cholestrol acyl transferase have active amino groups for conjugation. Cathepsin cysteine proteases and cytosolic phospholipase $A_2$ have numerous thiol groups for conjugation.

The presence within a combinatorial affinity labeling library of an affinity label molecule having the ability to specifically interact with and covalently bond to the macromolecular target may be indicated by comparing the rates of reactivity of the affinity labeling library both in the presence and absence of the macromolecular target.

The rates and number of members of the affinity labeling library that react with the macromolecular target can be determined by employing a variety of different spectroscopic, spectrophotometric and/or fluorescent assays, often monitored directly in a reaction tube or well.

For example, the activated functional group of the oligomeric affinity label may comprise a "leaving group" which is liberated upon covalent bond formation and which is readily detectable in solution subsequent to liberation. The rate of appearance of the detectable leaving group, either in the absence of spontaneous hydrolysis of the library, catalytic hydrolysis by the macromolecular target or corrected for either or both of these, may then serve as a quantitative indicator of the formation of covalent bonds between the affinity label and the macromolecular target.

The rate of appearance of the leaving group may be measured continuously and is indicative of both the rate of spontaneous hydrolysis and/or macromolecular target catalytic hydrolysis of the affinity label molecules and the rate of formation of a covalent adduct between the macromolecular target and the affinity label. To distinguish between the rate of spontaneous hydrolysis and the rate of formation of a covalent adduct between the macromolecular target and the affinity label, a comparison may be made between the observed rate of leaving group appearance both in the presence and absence of the target macromolecule; covalent bond formation with the target macromolecule will result in both a greater rate and extent of release of the leaving group. Thus, an increase in the rate of appearance of leaving group in the presence of a macromolecular target as compared to in the absence of a macromolecular target normally will be due primarily to covalent bond formation between the affinity label and the macromolecular target.

To distinguish between the rate of catalytic hydrolysis and the rate of formation of an adduct between the macromolecular target and the affinity label, one may block the active site of the macromolecular target, and a comparison can be made between the rate of appearance of leaving group in the presence of the blocked and of the unblocked macromolecular target.

Leaving groups can be selected such that their presence can be easily detected in solution. Thus, preferably, the leaving group is p-nitrophenolate anion or thiophenolate anion. p-Nitrophenolate anion is an excellent leaving group in that it is readily detectable in solution by spectrophotometry at 412 nm. Thiophenol anion also is an excellent leaving group in that it is readily detectable in solution by using the dithiol Ellman's Reagent (5,5'-dithiobis(2-nitrobenzoic acid)), which undergoes thiol exchange with thiophenol anion to give rise to a chromophore that absorbs maximally at 412 nm.

When leaving groups are not readily detectable in solution, the rate of reaction between members of the affinity labeling library and the macromolecular target may be determined by other means. For example, the affinity labels in the combinatorial library may be labeled with groups which are directly or indirectly detectable, such as fluorescers, radiolabels, chemiluminescers, specific binding pairs, such as biotin and strept/avidin, ligands and antibodies, e.g. digoxin and antidigoxin, and the like, where the protein of the specific binding pair may be labeled with the labels indicated above, as well as enzymes. For biotinylated libraries, covalent bonding of the affinity label to the macromolecular target may be established by demonstrating that the biotin label is associated with the macromolecular target even after vigorous washing and immunoblotting. Alternatively, boiling the biotinylated components remaining after washing and immunoblotting can provide unambiguous evidence that covalent bonding has occurred. Alternatively, one may capture the protein target with an antibody and after washing away non-covalenlty bound label, detect the presence of the label. Methods for detecting the covalent bonding of the affinity label to the target protein are readily developed in accordance with known techniques for detecting the presence of a label bound to a known protein.

Furthermore, in cases where a single macromolecular target is employed in the binding assays, a clear and unambiguous assessment of whether a covalent reaction has taken place can also be achieved using mass spectrometry. For example, the mass of the macromolecular target prior to being contacted with an affinity labeling library can be determined and compared to the mass of the macromolecular target subsequent to being contacted with the library. Increases in mass subsequent to contact with the affinity label library will normally be due primarily to covalent attachment of affinity labels to the target. Also, the macromolecular adduct may be fragmented and the mass of a fragment particularly associated with the affinity label may be determined by comparison of the mass of fragments of the unlabeled target with the mass of fragments of the labeled target.

Mass spectrometry may also be employed to provide a clear and unambiguous identification of the actual affinity label which bound to the macromolecular target in cases where only a limited number of monomer units of the oligomeric affinity label are unknown. For example, when the identity of only two amino acid monomers of an oligopeptide are unknown, the difference in mass for each of the possible pair-wise combinations of amino acids used to construct the library are often unique. By comparison to the bound macromolecule or a fragment thereof (assuming one equivalent of macromolecule and library reactant), one may readily determine the identity of the two unknown amino acids. From this determination, only two different affinity label molecules then need to be synthesized to determine the exact positions of the unknown amino acids. For more diverse libraries which have three unknown amino acids, in many instances only six oligopeptides need to be synthesized to determine the exact positions of the amino acids in the unknown oligopeptide. In cases where the unknown combinations of amino acids are not unique, tandem mass spectrometry can be used to determine the identity of the pair of amino acids or even the exact sequence of the unknown oligopeptide.

Confirmation that a particular affinity label specifically interacts with and covalently bonds to a macromolecular target of interest may be achieved by resynthesizing that particular affinity label and again assaying for its ability to covalently label the macromolecular target. For such confirmational assays, binding to the macromolecule can be measured directly using methods as described above including detecting the liberation of leaving group, detecting the formation of biotinylated macromolecule if the affinity label is biotinylated and mass spectrometry.

Any macromolecular adduct may also be fragmented and sequenced by MS/MS or other classical methods to determine the exact site of affinity label attachment or to determine the sequence of the actual affinity label that bound to the macromolecule. In cases where all members of a combinatorial affinity labeling library have the same activated functional group, those members exhibiting the fastest rate of covalent bond formation with a macromolecular target normally owe their enhanced reactivities primarily to the non-covalent specificity the oligomer exhibits for the macromolecular target site. All other things being equal (as is likely to be the case in a series of closely related structures), the greater the specific affinity of an affinity label for a macromolecular target site, the tighter the non-covalent interaction between the affinity label and that target site, and the faster the activated functional group of the affinity label forms a covalent bond with a proximally located reactive functionality on the macromolecular target. Thus, contacting an affinity labeling library with a macromolecule of interest not only allows for identification of affinity labels having a specific affinity for a macromolecular target site, but also of those affinity labels which non-covalently interact proximal to a reactive functionality on the macromolecule capable of covalent bond formation with the activated functional group.

Once an affinity label molecule or molecules that specifically label a macromolecular target are identified and selected, the functional group can be activated with a second activating moiety to produce affinity labels having a second activated functional group which is less reactive than the first activated functional group so as to produce new affinity labels which exhibit even greater specificity for labeling the macromolecular target. Implicit in this approach is the "reactivity-selectivity" principle which indicates that a label becomes more selective for its target if its inherent chemical reactivity is reduced. (See *Rates and Equilibria of Organic Reactions*, Leffler, J. E. and Grunwald, E., J. Wiley and Sons, New York, 1963, pgs. 162–168). If the first activated functional group of the affinity label comprises an aromatic ring such as phenyl, thiophenyl or benzyl alcohol, the aromatic ring may be substituted with different chemical groups at different sites to lower the inherent chemical reactivity of the second activated functional group.

Other variables may also be exploited to identify the most selective affinity label molecules present in the combinatorial library, under conditions in which more than one library member reacts with the target macromolecule. For example, the temperature at which the combinatorial library is contacted with the macromolecular target, the concentrations of the library components relative to the macromolecular target, and the time the library remains in contact with the macromolecular target can all be varied to modulate the overall reactivity of affinity label molecules. Means for varying these conditions will be well within the skill level in the art.

If a macromolecular target of interest possesses multiple reactive functionalities, one may determine which of those reactive functionalities can be specifically affinity labeled by member(s) of a combinatorial affinity labeling library. By "specifically affinity labeled" is meant that a functionality or limited number of functionalities on the macromolecular target are covalently bonded to an affinity label molecule whereas covalent bonding of other functionalities on the macromolecular target by that affinity label molecule is substantially absent in the environment in which the affinity label and the macromolecular target are combined. A combinatorial affinity labeling library will be contacted with a macromolecular target of interest having multiple reactive functionalities and the macromolecular adduct produced may be fragmented and the fragment carrying the label identified to determine the site of attachment for each affinity label molecule and the identity of the affinity label attached at each site. A complete map of the attachment sites on the macromolecular target and the affinity labels that bound at those sites is constructed and affinity labels which bind at only a single or limited number of sites are selected.

The oligomeric affinity label will desirably include a compound having a biological activity of interest. This biologically active compound may be joined to the affinity label at any convenient site, by a bond or a convenient linking group. Depending upon the nature of the biologically active compound, the linking group may provide for displacement in solution of the compound from the affinity label molecule by having a relatively long hydrophilic linking group having heteroatoms in the chain or as side groups, e.g. oxy, amino, oxo, carboxylate, etc. The linking group may be an amino acid or oligopeptide of from 2 to 6 amino acids, polyoxyalkylene of from 1 to 10 units, where allkylene is of from 2 to 3 carbon atoms, a sugar or the like.

The particular linking group employed will usually depend on the nature of the biologically active compound and its function.

The linking group may provide for a stable link between the biologically active compound and the affinity label molecule or for controlled release of the biologically active compound from the affinity label. By employing hydrolytically labile bonds under the conditions of use of the affinity label, the biologically active compound may be slowly released over an extended period of time. With use of an oligopeptide linking group recognized by a protease, there will be a continued release of the biologically active compound in accordance with the rate that the linking group is hydrolyzed.

The biologically active compound may be any compound for which there is a diagnostic, prophylactic or therapeutic interest, where one wishes to have an extended lifetime, and/or one may wish to change the distribution of the biologically active compound in vivo. Therefore, diagnostic compounds may include radiolabels, chelated or unchelated e.g., technetium, iodine, gadolinium, etc., compounds which provide for nuclear magnetic resonance, computer tomography, positron emission tomography, blood volume calculations, angiography, lymphography, etc. For prophylactic or therapeutic purposes, one may use a variety of drugs, particularly derived from prodrugs, where sites on the drug are known not to interfere with reactivity or one provides for slow release of the drug from the macromolecular compound. Compounds of interest include enzyme inhibitors, such as inhibitors of ACE, renin, thrombin, Factor Xa, xanthine oxidase, endothelin converting enzyme, farnesyl transferase; receptor inhibitors, such as receptors for interferon α, β, and γ, growth factors, e.g., EGF, TGF, PDGF, IGF1 and II, etc., hormone agonists and antagonists, such as insulin, erythropoietin, chorionic somatomammotropin hormone, luteinizing hormone, and thyrotropin.

Indications which may be treated include, embolisms, hypertension, congestive heart failure and tumor angiogenesis (cancer). Specific drugs of interest include argatroban, 4-(S)-amino-5-cyclohexyl-3-(S)-hydroxypentanoic acid (ACHPA), cyclic RGDDFV, where DF intends D-phenylalanine, etc.

Numerous utilities arise from the ability to identify affinity labels which bind to a macromolecule of interest in a site-specific manner. For example, site-specific affinity labels find use in defining sites on various targets that, when blocked by an affinity label, results in a loss of activity of the target. These labels may find usefulness as therapeutics, i.e., as enzyme inhibitors, receptor antagonists, or the like. Site-specific affinity labels also allow for directing biologically active compounds to specific sites in vivo, including tumorigenic sites, thereby localizing the biologically active compound to a desired site in vivo while being substantially absent from other potential target sites. Finally, biologically active compounds may be specifically directed to long-lived blood components, thereby increasing the effective half-life of the biologically active compound in the vasculature.

Thus, there exist a multitude of useful applications for affinity label molecules and the combinatorial affinity labeling libraries described herein. These applications include, but are not limited to, agonism and antagonism at biological receptors, attaching biologically active molecules to specific target sites in vivo for the purpose of increasing the half-life of said biologically active molecules, labeling macromolecules for premature destruction, directing biologically active molecules to specific sites in vivo and exploiting numerous sites that have been hitherto difficult to target including tumorigenic-specific sites. These applications have profound implications for drug design and discovery, including the generation of specific linkages to specific sites on various living cells and tissues.

Regarding enzyme inhibition, site-specific labeling of macromolecules affords the possibility of labeling enzymes at sites that are distal to catalytic sites, yet capable of abolishing enzyme activity by blocking channels through which substrates must traverse (i.e., cyclooxygenases), or preventing obligatory movements of flaps associated with enzyme structure (i.e., HIV protease), or otherwise preventing the ability of catalytic enzymes to function as "chemical machines" by blocking movements of their component parts which are required for enzyme activity.

The following examples are offered by way of illustration and are not intended in any way to limit the invention described herein.

EXPERIMENTAL

EXAMPLE 1

Construction of N-acetyl Glutamic Acid-Containing Affinity Labeling Libraries

Two N-acetyl glutamic acid-containing peptidyl affinity labeling libraries were designed and constructed for use in screening for specific affinity labeling of macromolecular targets. The structure of these two affinity labeling libraries is described as follows:

Affinity Labeling Library Number 1:

| Structure | No. Compds per Well | No. Wells |
| --- | --- | --- |
| Ac-Glu(p-OC$_6$H$_4$NO$_2$)-O$_1$-Q$_2$-X$_1$-X$_2$-NH$_2$ | 200 | 100 |

Affinity Labeling Library Number 2:

| Structure | No. Compds per Well | No. Wells |
| --- | --- | --- |
| Ac-Glu (SC$_6$H$_5$)-O$_1$-Q$_2$-X$_1$-X$_2$-NH$_2$ | 200 | 100 |

In each of the two above described structures, $X_1$ and $X_2$ represent any one of 10 selected amino acids in the L-configuration, $O_1$ represents any one of 10 selected amino acids in the L-configuration and $O_2$ represents any one of 10 selected amino acids in the D-configuration.

The L-amino acids $X_1$, $X_2$ and $O_1$ were carefully selected to maximize diversity while minimizing any potential interference that may occur with the activated functional group of the affinity label molecule. The D-amino acids $O_2$ were carefully selected in order to prevent facile peptidyl cleavage in vivo and to maximize the non-covalent interactions of the affinity label with the macromolecular targets.

In each of the two affinity labeling libraries identified above, the ten amino acids selected for each of the groups $X_1$, $X_2$, $O_1$, and $O_2$ are shown in Table I.

TABLE I

| Amino Acid | Characteristic | Starting material |
| --- | --- | --- |
| Glutamic acid | acidic | Fmoc-Glu(OtBu)-OH |
| Glutamine | amide | Fmoc-Gln(Trt)-OH |
| Histidine | basic | Fmoc-His(Trt)-OH |
| Arginine | basic | Fmoc-Arg(Pmc)-OH |
| Methionine | sulfide | Fmoc-Met-OH |
| Serine | alcohol | Fmoc-Ser(tBu)-OH |
| Tyrosine | phenol | Fmoc-Tyr(tBu)-OH |
| Leucine | aliphatic | Fmoc-Leu-OH |
| Phenylalanine | aromatic | Fmoc-Phe-OH |
| Tryptophan | aromatic | Fmoc-Trp(Boc)-OH |

The ten amino acids shown in Table I were selected for constructing the oligopeptides of the affinity labeling libraries described herein first to maximize the diversity of the α-side chain of the members of the affinity labeling libraries and, second, to minimize any potential interference which may occur between the α-side chain and the activated functional groups.

The two combinatorial affinity labeling libraries described above were constructed as follows:

Synthesis of the above two N-acetyl glutamic acid-containing affinity labeling libraries utilized standard Merrifield solid phase peptide synthesis method employing F-moc chemistry which is well known in the art. The methodology of peptidyl resin mixing and splitting was used during the process.

Specifically, a schematic illustration outlining the construction of the two N-acetyl glutamic acid-containing affinity labeling libraries described above is shown in FIG. 1. In step (1) shown in FIG. 1, each of the ten different F-moc-protected L-amino acids shown in Table I were individually linked to an identical amount of resin support. This gives rise to ten equimolar independent and distinct pools of a single amino acid coupled to a resin support.

Coupling of the F-moc-protected L-amino acids to the resin support was performed by adding to the resin in a reaction vessel with a N,N-dimethyl formamide (DMF) solution of the L-amino acid (4 equivalents), O-benzotriazol-1-yl-N,N,N',N'-tetramethyl-uronium hexafluorophosphate (HBTU) (4 equivalents), 1-hydroxybenzotriazole (HOBt) (4 equivalents) and diisopropylethyl amine (DIEA) (8 equivalents). The reactions were allowed to proceed for 1.5 hours at room temperature. Completion of each reaction was monitored by a ninhydrin test. The coupling reactions were repeated until the ninhydrin test for each reaction was negative. Once coupling was complete as evidenced by a negative ninhydrin test, the peptidyl resin in each of the ten separate reactions was washed with N-methyl 2-pyrrolidinone (NMP).

Figure 1:
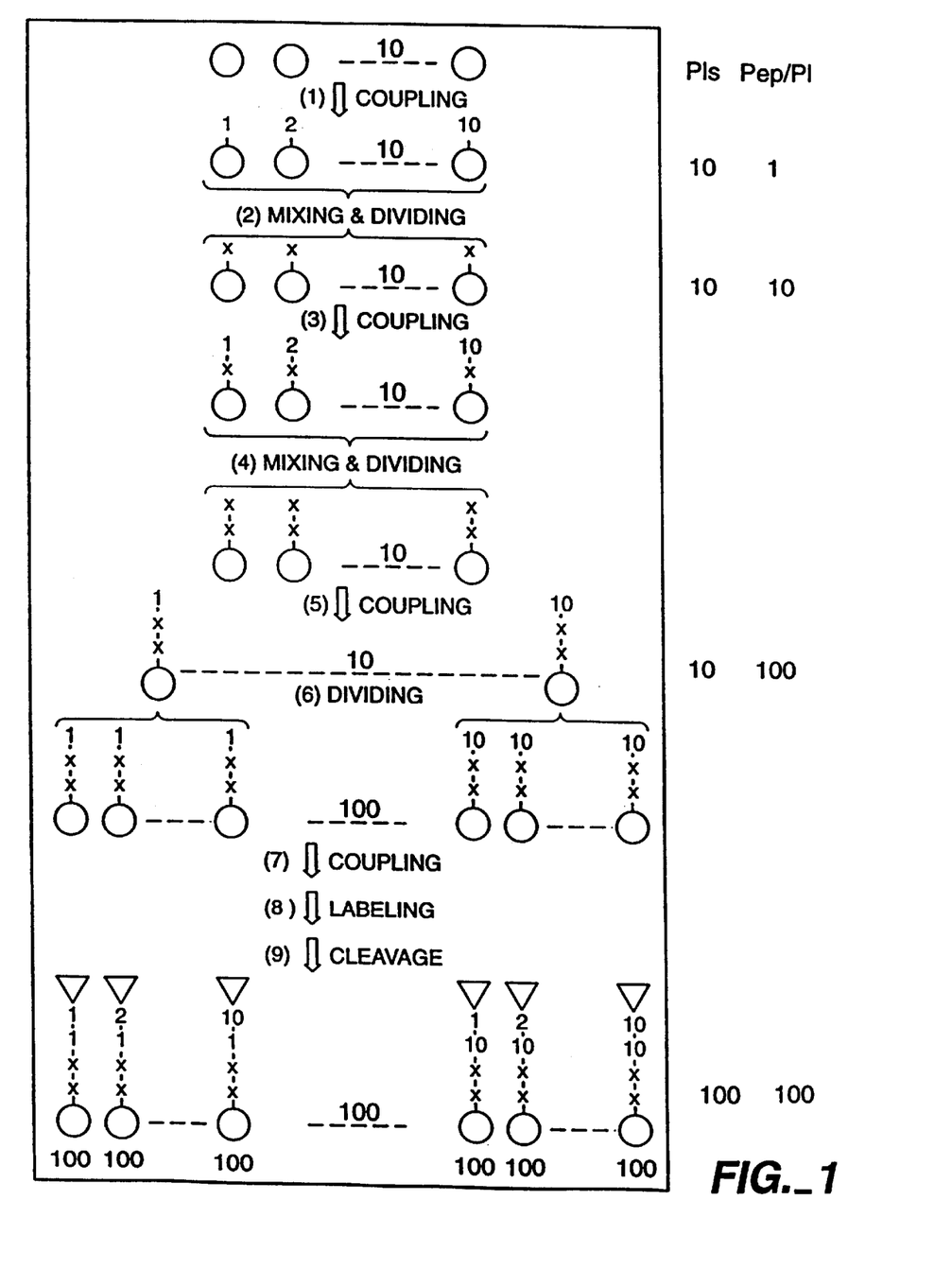
FIG. 1 presents a schematic illustration outlining the construction of the two N-acetyl glutamic acid-containing soluble affinity labeling libraries presented in Example 1. Each step in the construction of the affinity labeling libraries is identified in the figure as a number in parentheses. "Pls" refers to the number of peptide-containing pools present at various steps during the construction of the libraries. "Pep/Pl" refers to the number of peptides in each pool at various steps during the construction of the affinity labeling libraries.

As shown in step (2) of FIG. 1, the resins from each of the ten independent and distinct pools generated in step (1) were then mixed and divided into ten identical pools. This gives rise to ten identical pools each consisting of the ten distinct L-amino acids singly linked to the resin support. Before the second L-amino acids were coupled to the resin support bearing ten independent and distinct pools of a single F-moc-protected amino acid coupled to a resin support, the F-moc entities protecting the amino groups of the resin-bound amino acids were removed by treating with 20% piperidine in NMP twice, 2 minutes and 15 minutes, respectively at room temperature. The resin in each of the ten independent and distinct pools was then washed with NMP.

As shown in step (3) of FIG. 1, each of the ten identical pools generated in step (2) was then coupled to one of the ten f-moc-protected L-amino acids shown in Table I. Coupling reactions were again carried out by adding to each of the ten identical pools a DMF solution of the L-amino acid (4 equivalents), HBTU (4 equivalents), HOBt (4 equivalents) and DIEA (8 equivalents). Again, the reactions were allowed to proceed for 1.5 hours at room temperature at which time each reaction was monitored by a ninhydrin test. The coupling reactions were again repeated until the ninhydrin test for each reaction was negative. Once coupling was complete as evidenced by a negative ninhydrin test, the peptidyl resin in each of the ten separate reactions was washed with NMP.

The result of this second round of coupling is the generation of ten equimolar independent and distinct pools of dipeptides linked to a resin support. As shown in FIG. 1, since each of the ten independent and distinct pools contains ten distinct dipeptides, there are now generated a total of 100 distinct dipeptides.

As shown in step (4) of FIG. 1, the resins from each of the ten independent and distinct pools generated in step (3) were mixed and then divided into ten identical pools. This gives rise to ten identical pools each consisting of one hundred distinct dipeptides linked to the resin support. Before the third round of coupling, the F-moc entities protecting the amino groups of each of the resin-bound dipeptides were removed by treating with 20% piperidine in NMP twice, 2 minutes and 15 minutes, respectively at room temperature.

As shown in step (5) of FIG. 1, each of the ten identical pools generated in step (4) is coupled to one of the ten F-moc-protected amino acids shown in Table I. In this round of coupling, unlike all of the other rounds of coupling, amino acids in the D-configuration are employed. Coupling reactions were again carried out by adding to each of the ten identical pools a DMF solution of the amino acid (4 equivalents), HBTU (4 equivalents), HOBt (4 equivalents) and DIEA (8 equivalents). Again, the coupling reactions were allowed to proceed for 1.5 hours at room temperature at which time each reaction was monitored by a ninhydrin test. The coupling reactions were again repeated until the ninhydrin test for each reaction was negative. Once coupling was complete as evidenced by a negative ninhydrin test, the peptidyl resin in each of the ten separate reactions was washed with NMP.

The result of this third round of coupling is the generation of ten equimolar independent and distinct pools of tripeptides linked to a resin support. As shown in FIG. 1, since each of the ten independent and distinct pools contains one hundred distinct tripeptides, there are now generated a total of 1000 distinct tripeptides.

As shown in step (6) of FIG. 1, each of the ten independent and distinct pools of tripeptides generated in step (5) were each divided into a set of ten identical pools without mixing the pools before dividing. This gives rise to ten sets of ten identical pools (100 pools total, only ten of which are distinct) each containing 100 tripeptides. The step of splitting the pools without mixing allows for the identity of the third and fourth amino acids coupled to the resin to be known. Before the fourth round of coupling, the F-moc entities protecting the amino groups of each of the resin-bound tripeptides were removed by treating with 20% piperidine in NMP twice, 2 minutes and 15 minutes, respectively at room temperature. The resin in each of the ten independent and distinct pools was then washed with NMP.

As shown in step (7) of FIG. 1, each of the ten identical pools in each of the ten sets of pools generated in step (6) was then coupled to one of the ten F-moc-protected L-amino acids shown in Table I. Coupling reactions were again carried out by adding to each pool a DMF solution of the L-amino acid (4 equivalents), HBTU (4 equivalents), HOBt (4 equivalents) and DIEA (8 equivalents). Again, the reactions were allowed to proceed for 1.5 hours at room temperature at which time each reaction was monitored by a ninhydrin test. The coupling reactions were again repeated until the ninhydrin test for each reaction was negative. Once coupling was complete as evidenced by a negative ninhydrin test, the peptidyl resin in each of the ten separate reactions was washed with NMP.

The result of this fourth round of coupling is the generation of one hundred equimolar independent and distinct pools of tetrapeptides linked to a resin support. As shown in FIG. 1, since each of the one hundred independent and distinct pools contains one hundred distinct tetrapeptides, there are now created a total of 10,000 distinct tetrapeptides.

Following this fourth round of coupling, the F-moc entities protecting the amino groups of each of the resin-bound tetrapeptides were removed by treating with 20% piperidine in NMP twice, 2 minutes and 15 minutes, respectively at room temperature followed by washes with NMP.

In both affinity labeling library numbers 1 and 2 described herein, L-glutamic acid was employed as a source of a functional group for activation. Specifically, in affinity labeling library numbers 1 and 2, the L-glutamic acid derivative employed was N-acetyl glutamic acid.

As shown in step (8) of FIG. 1, each of the one hundred independent and distinct pools generated in step (7) were coupled to N-acetyl glutamic acid for the purpose of providing a functional group for activation. For coupling of N-acetyl glutamic acid to the 100 independent and distinct pools of tetrapeptides generated in step (7), N-acetyl glutamic acid (8 equivalents) and dicyclohexylcarbodiimide (DCC) were dissolved in a minimum amount of dichloromethane (DCM) individually and cooled at 0° C. This solution was stirred at 0° C. for 0.5 hour allowing for the formation of a precipitate. After filtering the precipitate in dicyclohexylurea (DCU), the cold and clear solution was added individually to the 100 separate and distinct pools of resin-bound tetrapeptides generated in step (7). The reaction was completed in 2 hours as evidenced by a negative ninhydrin test. Upon the completion of the coupling reaction evidenced by a negative ninhydrin test, and the peptidyl resin was washed with NMP.

In coupling N-acetyl glutamic acid anhydride with each of the 100 independent and distinct pools of tetrapeptides generated in step (7), the nucleophilic attack of the free α-amino function of the resin-bound tetrapeptide at the two different electrophilic sites of N-acetyl glutamic acid anhydride is relatively indiscriminate. This indiscriminacy results in amide formation at either the α-carboxyl group or the γ-carboxyl group of the N-acetyl glutamic acid entity. As a result, two different products are formed for each member of the library; one where the linkage is through the α-carboxyl of the N-acetyl glutamic acid entity and the other where the linkage is through the γ-carboxyl. Therefore, in affinity labeling library numbers 1 and 2, each independent and distinct pool of the library actually contains 200 different compounds as is shown above.

Upon completion of the coupling of N-acetyl glutamic acid entity to the 100 independent and distinct tetrapeptide pools generated in step (7), the remaining free carboxyl of the glutamyl group (which, as described above, may be either an α-carboxyl or a γ-carboxyl group) is activated. Either p-nitrophenolate (affinity labeling library number 1) or thiophenolate (affinity labeling library number 2) was employed to activate the free carboxyl of the glutamyl group.

p-Nitrophenolate and thiophenolate were selected for use as activating groups because they exhibit certain advantageous properties.

First, both p-nitrophenol and thiophenol possess significant advantages with regard to detection upon liberation as a leaving group after covalently binding to a macromolecule target site of interest. For example, the p-nitrophenol leaving group has a distinctive UV absorption that can be easily detected. The thiophenol leaving group can form an adduct with Ellman's reagent which also can easily be detected by UV spectrometry. These properties make p-nitrophenolate and thiophenolate excellent candidates for activating groups.

Furthermore, activation of the free glutamyl carboxyl with either p-nitrophenolate or thiophenolate results in affinity labels having a desirable reactivity. These activated functional groups are both quite reactive, which ensures covalent bond formation with a macromolecular target if a target nucleophilic functionality, like a primary amine, is brought into close proximity to the activated functional group. However, the p-nitrophenolate and thiophenolate activated carboxyl groups are not so reactive that they will form a covalent bond with other available nucleophiles.

Finally, these activated functional groups also have reasonable stability in most organic solutions, in aqueous solutions below pH 7.0 and under normal storage conditions.

Activation of the free glutamyl carboxyl with p-nitrophenolate (affinity labeling library number 1) or thiophenolate (affinity labeling library number 2) was carried out as follows. An NMP and DCM (1:4) solution of either p-nitrophenol or thiophenol (10 equivalents) and N,N'-diisopropylcarbodiimide (DIC) (10 equivalents) was added to the free acid-peptidyl resin in a reaction vessel. The reaction was allowed to proceed for 2 hours at room temperature at which time the resin was washed with NMP. The labeling entity coupling reaction was then repeated to ensure completion. The result of this step (8), therefore, was the generation of 100 independent and distinct pools of tetrapeptides bound by an N-acetyl glutamic acid group wherein either the α- or γ-carboxyl is activated by p-nitrophenolate (affinity labeling library number 1) or thiophenolate (affinity labeling library number 2). Each of the 100 independent and distinct pools, therefore, possesses 200 different resin-bound peptidyl components.

Finally, to complete the construction of the affinity labeling libraries, as shown in step (9) of FIG. 1, the completely constructed affinity labeling peptides were cleaved from the resin component to which they were bound and were purified. Cleavage from the resin and purification of the libraries was performed as follows.

The peptidyl resin mixtures in each of the 100 independent and distinct pools generated in step (8) were dried. Each was then independently treated with trifluoroacetic acid (TFA)/$H_2O$ (95/5, v/v) for 1.5 hours. This results in cleavage of the peptides from the resin and deprotection of the amino acid side chains. The peptide/TFA solution was then extracted twice with ether. Following ether extraction, the peptide solution was lyophilized giving rise to the completely constructed and dried affinity labeling library.

The final combinatorial affinity labeling library exhibits minimal interactions between the individual peptidyl components in the library and is substantially stable under normal storage conditions.

The above description details the construction of affinity labeling libraries numbers 1 and 2. Other affinity labeling libraries have also been constructed in exactly the same manner as described above except that a different method was used for coupling the L-glutamic acid residue to the resin-bound tetrapeptides generated in step (7) of FIG. 1.

Specifically, rather than employing N-acetyl glutamic acid anhydride in the coupling reaction of step (8) in FIG. 1, one may employ N-acetyl glutamic acid γ-9-fluorenemethyl ester. The reaction conditions for this coupling were identical to those described above for the coupling of F-moc amino acids to the peptidyl resin as in step (7) shown in FIG. 1.

Once coupled to the resin-bound tetrapeptides generated in step (7) of FIG. 1, the 9-fluorenemethanol group was subsequently removed thereby freeing the γ-carboxyl side chain which was then used as an activation site. Activation, cleavage of the peptidyl affinity labels from the resin support and purification of the combinatorial affinity labeling libraries were then performed as described above.

EXAMPLE 2

Construction of N-Biotinyl Glutamic Acid-Containing Affinity Labeling Library

One N-biotinyl glutamic acid-containing peptidyl affinity labeling library was designed and constructed for use in screening for specific affinity labeling of macromolecular targets. The structure of this affinity labeling library is described as follows:

| Affinity Labeling Library Number 3: | | |
|---|---|---|
| Structure | No. Compds per Well | No. Wells |
| Biotin-Glu(SC$_6$H$_5$)-O$_1$-O$_2$-X$_1$-X$_2$-NH$_2$ | 200 | 100 |

As described in Example 1, in the above disclosed structure, $X_1$ and $X_2$ represent any one of 10 amino acids in the L-configuration, $O_1$ represents any one of 10 selected amino acids in the L-configuration and $O_2$ represents any one of 10 selected amino acids in the D-configuration. The 10 amino acids employed herein were the 10 amino acids set forth in Table I.

The N-biotinyl glutamic acid-containing affinity labeling library was constructed essentially as described above in Example 1 and as diagramed in FIG. 1. However, for coupling of the resin-bound tetrapeptides in each of the 100 independent and distinct pools to the L-glutamic acid derivative in step (8) of the process described in Example 1 and shown in FIG. 1, rather than employing an N-acetyl glutamic acid entity as was done in Example 1, we herein employed a N-biotinyl glutamic acid γ-9-fluorenemethyl ester entity.

N-biotinyl glutamic acid γ-9-fluorenemethyl ester was prepared as follows. A fine powder of glutamic acid (100 mmol) was suspended in dry tetrahydrofuran (THF) (100 mL), then 1 M triethylborane (BEt$_3$) in THF (120 mmol) was added. This suspension was heated to reflux until it completely turned to solution. The solution was then filtered followed by the addition of toluene to initiate precipitation. A white powder product (boroxazolidone of glutamic acid) was obtained at a yield of 89%.

Boroxazolidone of glutamic acid (95 mmol) and 9-fluorenemethanol (91 mmol) were then dissolved in dichloromethane (500 mL). The solution was stirred and chilled in an ice bath. Dimethyl aminopyridine (DMAP) (7 mg) was added, followed by the addition of dicyclohexylcarbodiimide (DCC) (20 mg) in DCM (25 mL). After the mixture was stirred for 2 hours at 0° C., DCU was filtered. The filtrate was diluted with DCM (800 mL) and was then washed with 2.5% sodium bicarbonate and water. The organic layer was dried over MgSO$_4$ and treated with hydrogen chloride gas. The white precipitate (glutamic acid g-9-fluorenemethyl ester) was collected and washed with THF. The yield was 60%.

Finally, glutamic acid γ-9-fluorenemethyl ester (1.5 g) and DIEA (2 equivalents) were dissolved in dry N,N-dimethyl formamide (DMF) (30 mL). The solution was stirred at 5° C. and biotinyl chloride (prepared in situ from biotin and $SOCl_2$) dissolved in dry DMF (3 mL) was added. After stirring at room temperature for 4 hours, DIEA (0.5 equivalent) was added. After 1 hour, another portion of DIEA (0.5 equivalent) was added. After another hour, the solution was added slowly to a saturated NaCl solution (250 mL). Precipitate was allowed to form which was collected, filtered and dried. The solid was then extracted with 3×50 mL of methanol. The extracted solution was then concentrated and a light yellow oil (1.8 g) was passed through a silica gel column with $EtOAc/CH_3OH/HOAc$ (85/15/1). The white solid product (0.52 g) was obtained and represented N-biotinyl glutamic acid γ-9-fluorenemethyl ester.

n-Biotinyl glutamic acid γ-9-fluorenemethyl ester was then coupled to each of the one hundred independent and distinct pools of resin-bound tetrapeptides generated in step (7) shown in FIG. 1. For coupling of N-biotinyl glutamic acid γ-9-fluorenemethyl ester to the 100 independent and distinct pools of tetrapeptides generated in step (7), N-biotinyl glutamic acid g-9-fluorenemethyl ester (8 equivalents) and DCC were dissolved in a minimum amount of DCM individually and cooled at 0° C. This solution was stirred at 0° C. for 0.5 hour. After filtering the precipitate in DCU, the cold and clear solution was added individually to the 100 separate and distinct pools of tetrapeptides generated in step (7). After 2 hours, the reaction was monitored by a ninhydrin test and the coupling reaction was continued until the ninhydrin test was negative. At the completion of the coupling reaction evidenced by a negative ninhydrin test, the peptidyl resin was washed with NMP.

Upon completing the coupling of N-biotinyl glutamic acid g-9-fluorenemethyl ester to the 100 independent and distinct tetrapeptide pools generated in step (7), the 9-fluorenemethanol group was removed from the γ-position, thereby freeing up a γ-carboxyl side chain which was then used as an site for activation. In this case, the free γ-carboxyl was activated as described above with thiophenolate.

Finally, cleavage of the activated affinity label peptides from the resin support and purification of the affinity labeling library was also performed as described above in Example 1.

The final affinity labeling library product exhibits minimal interactions between the individual peptidyl components in the library and is stable under normal storage conditions.

EXAMPLE 3

Construction of a Solid Phase Affinity Labeling Library

One solid phase peptidyl affinity labeling library w as designed and constructed for use in screening for specific affinity labeling of macromolecular targets. The structure of this solid phase affinity labeling library is similar to affinity labeling library number 2, but on a solid support and is prepared as follows

| Biotin-Containing Solid Phase Affinity Labeling Library Number 4: | | |
|---|---|---|
| Structure | No. Compds per Well | No. Wells |
| $O_1$-$O_2$-$X_1$-$X_{2\text{-Resin}}$ Ac-Glu($SC_6H_5$)- | | |

As described in Examples 1 and 2, in the above disclosed structure, $X_1$ and $X_2$ represent any one of 10 amino acids in the L-configuration, $O_1$ represents any one of 10 selected amino acids in the L-configuration and $O_2$ represents any one of 10 selected amino acids in the D-configuration. The 10 amino acids e mployed herein were the 10 amino acids set forth in Table I.

The synthesis of this library is similar to that for affinity labeling library number 3, except (1) a TFA stable PEG-resin was used and (2) coupling of α-carboxyl of $N^α$-acetyl-$O^γ$-Fmoc-glutamic acid was specifically effected to provide the N-terminal amino acid residue in the 100 compounds per pool library (see Example 2 for the description of this step.) At the end of the synthesis, the protected peptidyl resin was treated with 95% TFA for one hour, when all of the side chain protecting groups on the peptide were removed, while the peptides remained bound to the resin.

EXAMPLE 4

Construction of a Biotin-Containing Solid Phase Solid Phase Affininity Labeling Library Another solid phase affinity labeling library was designed and constructed in which biotin is contained at the N-terminus and the activated thioester is located at the C-terminus on the resin. The structure is described as follows:

| Structure | No. Compds per Well | No. Wells |
|---|---|---|
| Biotin-$O_1$-$O_2$-$X_1$-$X_2$-$SC_6H_4$CO-Resin | 100 | 100 |

The construction of this biotin-containing solid phase affinity labeling library comprises four steps.

The first step is the synthesis of side chain protected peptide acid biotin-$O_1$-$O_2$-$X_1$-$X_2$-OH on the solid phase. The low concentration TFA solution labile chlorotrityl resin was used. The procedure for assembly of the peptide library is similar to the previous example, but in the last step biotin acid is used, instead of glutamic acid derivative.

In the second step, the side chain protected peptide acid is cleaved from the solid phase by treatment with acetic acid, 2,2,2-trifluoroethanol and dichloromethane (1:1:8 by volume) solution for 0.5 hr.

The third step is to couple the side chain protected peptide acid to a mercaptobenzoic resin with 1 eq. of HBTU, 1 eq. of HOBt and 2 eq. of DIEA for 2 hr.

The final step is the removal of all side chainprotected groups from the peptidyl resin with 95% TFA in water. After drying in vacuo, the peptidyl resin is ready for assay.

EXAMPLE 5

Assays using Affinity Labeling Libraries for the Purpose of Detecting the Formation of a Covalent Adduct Peptidyl affinity labeling libraries are formulated as 0.004 M solutions in dimethyl sulfoxide (DMSO). Approximate average molecular weights for the members of the libraries are based on the sum of the molecular weights of the known moieties of the compounds and an average value for the molecular weight of the amino acids that are varied. The compounds, in their lyophilized form, are weighed gravimetrically, and volumes of DMSO are added to the weighed compounds to give the specified concentration of 0.004 M using the calculated molecular weight as representative of that of the compounds. The resulting solutions are transferred to individual wells of polypropylene 96-well microtiter plates and stored at −20° C.

Reaction mixtures are prepared by first adding to the individual wells of a microtiter plate 0.002 mL of the individual solutions that comprise the library; the final concentration of the library is 0.08 mM in a volume of 0.1 mL. The microtiter plates are obtained from NUNC (MaxiSorp F8 framed). In separate polypropylene tubes, buffered solutions that either do or do not contain the target protein, which is either glycophorin A (GPA) or Human Serum Albumin (HSA), are prepared. These solutions contain the following components, and the concentrations given are those for the final reaction mixture: 10 mM phosphate, pH 7.4, 137 mM NaCl, 2.7 mM KCl and, when applicable, either 1.7 $\mu$M target protein, 0.5 mM 5,5'-dithiobis(2-nitrobenzoic acid) (Ellman's Reagent) or both.

Labeling reactions are initiated by the addition of the buffered solutions described above. Labeling reaction mixtures that result in a covalent adduct with the target protein also result in the release of either p-nitrophenol or thiophenol as the leaving group. Both of these molecules, which are referred to as the respective leaving group of the two libraries, are detectable by spectrophotometry either directly at 412 nm in the case of the p-nitrophenol or indirectly in the case of thiophenol by using the dithiol Ellman's Reagent, which undergoes thiol exchange with the thiophenol anion to give a chromophore that absorbs maximally at 412 nm.

The appearance of the leaving group can be measured continuously and, in the most general case, is indicative of both the rate of spontaneous hydrolysis of the library and the rate of formation of a covalent adduct between the target protein and a member or members of the library. To distinguish between the rates of spontaneous hydrolysis and adduct formation between the macromolecular target and affinity label molecules, a comparison is made between the observed rate of leaving group appearance both in the presence and absence of the target protein; reaction with the target protein results in both a greater rate and extent of release of the leaving group. The spectrophotometric method described above does not distinguish between a mechanism describing a target-protein dependent enhancement of the hydrolysis reaction and the actual formation of a covalent adduct. However, a method of distinguishing between these two mechanisms for the release of leaving group that is dependent on the presence of target protein will be described below.

Affinity labeling libraries that contain biotin as an integral part of each affinity label of the library have been constructed. Experimentally, the presence of biotin allows for the detection of the covalent adduct to the target protein after the adduct is formed. Preliminary experiments utilizing simple esters of biotin indicate that these esters will react with the surface of commercially available microtiter plates, and the reaction results in a modified plate that gives a significant signal for the detection of biotin. This is undesirable and represents a background level of biotinylation that would be problematic when trying to distinguish between a target-protein dependent reaction and a simple reaction of the biotinylated library with the plate, which is not interesting. The reaction of the thiophenol ester of biotin with NUNC MaxiSorp FS plates is dramatically reduced by treating the plates with a solution of iodomethane in DMSO (5% v/v; 0.2 mL per well of the plate, covered, 24 h at room temperature in the dark). The treated plates are rinsed extensively with Milli-Q water and then washed three times with 0.2 mL of 1% Tween-20 in Milli-Q water. The washed plates are then dried, and DMSO solutions of the library are added directly to the dry plate. As described above, labeling reactions with a biotinylated library are initiated by the addition of buffers that either do or do not contain target protein, and the release of leaving group is detected spectrophotometrically. At a predetermined time, which is typically 1 hour for initial screening experiments, the reaction mixture is aspirated off and the wells of the plate are immediately washed three times each with 0.02 mL of a solution of phosphate buffered saline (PBS;137 mM NaCl, 2.7 mM KCl, 10 mM Pi, pH 7.4). Previous experiments using monoclonal antibodies that are specific for binding to GPA show that during the labeling reaction, GPA binds to the iodomethane treated plates in a manner that prevents bound GPA from being removed during the washing steps.

The presence of biotin on the washed plate is determined as follows. A solution of PBS containing bovine serum albumin (BSA) at a concentration of 1% (w/v) is added to the wells of the plate (0.2 mL per well). The plate is then covered and either kept at room temperature for 2 hours or greater or at 4° C. overnight. The presence of BSA results in the coating of the wells of the plate with BSA, and coating of the wells by BSA prevents the non-specific binding of the protein conjugate avidin-horse radish peroxidase (Av-HRP), which is added during a subsequent step of the procedure. The solution of BSA in PBS is aspirated off, and the blocked plate is washed three times with 0.2 mL per wash of PBS/0.1% BSA/0.1% Tween-20. A solution of Av-HRP in PBS/0.1% BSA/0.1% Tween-20 is prepared to the specification of the manufacturer of the conjugate protein, and 0.1 mL of this solution is added to each well of the plate. The plate is covered and incubated for 0.5 hour at room temperature. During this time, the avidin portion of the protein conjugate binds to any biotin that is present in the well. The binding of avidin to biotin is one of the strongest binding reactions known in biochemistry; an equilibrium dissociation constant of $10^{-15}$ M describes the thermodynamic stability of the avidin-biotin complex. The binding reaction of avidin to biotin is complete after 0.5 hour, the wells of the plate are washed three times again with 0.2 mL per wash of PBS/0(.1% BSA/01% Tween-20). A solution of commercially prepared substrate for the HRP enzyme portion of the protein conjugate is added to each well (0.1 mL per well), and any enzyme that is present in a given well, by virtue of the avidin portion of the protein conjugate binding to biotin of the well, converts the substrate into products of which one has a strong absorbance at 650 nm. The appearance of this blue product is measured continuously for 0.5 hour, and after this time the wells are acidified by the addition of 0.1 mL of 1 N HCl. Acidification of the reaction mixture both stops the reaction, which is already virtually complete, and converts a product of the reaction from a blue color to a yellow color that has a maximal absorbance at 450 nm. The plate, after treatment with acid, is read at 450 nm to give endpoint values for the reactions occurring in the individual wells.

The experimental procedures described above give either indirect indications of the occurrence of a labeling reaction, which is the case when only the release of leaving group is measured, or the indirect observation of the formation of a covalent adduct which contains biotin. The presence of biotin on the target protein can be determined independently either by mass spectrometry, which represents a direct determination, or by submitting portions of the reaction mixtures to analysis by sodium dodecyl sulfate polyacrylamide gel electrophoresis (SDS-PAGE) followed by western blotting techniques that visualize where on the gel the biotinylated protein resides. The latter techniques are simple and fast in their execution.

For the analysis by SDS-PAGE, a portion of the actual reaction mixture is mixed with gel-sample loading buffer and heated at 100° C. for approximately 5 minutes and then applied to a SDS-PAGE, which is then developed by the application of an electric current across the gel, and this results in the separation of the protein components of the mixture on the basis of the molecular weights of those components. The proteins contained within the gel are then transferred from the gel's matrix to a sheet of nitrocellulose paper, which reacts with the proteins upon their contact with the sheet; the reaction gives covalently immobilized proteins on the sheet. The sheet is then incubated in a solution of PBS containing 5% (w/v) of powdered non-fat dry milk, which bind to and reacts with the portions of the sheet that do not already contain protein from the gel, and this "blocking of the blot" prevents further binding of proteins, which are added during subsequent steps of the procedure, to the sheet. The blocked sheet is washed with a PBS/1% milk solution and then a solution of either Av-HRP, polyclonal antibody or monoclonal antibody—the antibodies are specific to bind to the target protein—is added. The sheet is incubated with the solution for either 0.5 hour, in the case of Av-HRP, or 1 hour, in the cases of the antibodies, and then washed as described above to remove unbound Av-HRP or monoclonal an body; binding of these proteins to the sheet results from the specific biochemical interactions that these proteins have with their respective ligands (either biotin or the epitope(s) of the target molecule). The washed sheet that was probed with Av-HRP is then developed by the addition of $H_2O_2$, 3,3'-diaminobenzidine and $CoCl_2$ in 0.05 M Tris buffer, pH 7.6. The HRP enzyme portion of the conjugate catalyzes the formation of a darkly colored and insoluble product that accumulates on and near the protein to which the Av-HRP is bound. Sheets that were first probed with either of the two antibody types are next probed with a secondary antibody, which is both specific to bind to antibodies present on the sheet and also is a conjugate protein containing the catalytic activity of the enzyme HRP. The binding of secondary antibody is complete after 0.5 hour, and the sheet is then washed to remove secondary antibody that is not bound specifically to either the polyclonal or monoclonal antibody. The presence of HRP activity on the sheet, which is the result of the specific binding of the secondary antibody to the sheet via the target protein, is detected as described above. Detection of HRP activity when probing with antibodies identifies where on the gel the target protein migrates. By using both Av-HRP and antibodies, the experimentalist can ascertain that verify that a covalent modification to the target protein has taken place. The conditions for the preparation of modified target protein for SDS-PAGE analysis are harsh; these are reducing conditions in the presence of detergent at high temperature. It is highly unlikely that a non-covalent interactions) between a member of a biotin-containing library and a given target protein would persist during the preparation of the sample for SDS-PAGE.

EXAMPLE 6

Assays using Affinity Labeling Libraries for the Purpose of Detecting the Formation of a Covalent Adduct with Human Serum Albumin (HSA)

Microtiter plates (NUNC Maxisorp F96) are coated overnight at 4° C. with 0.1 mL/well of a solution of PBS (10 mM Pi, pH7.4, 137 mM NaCl, 2.7 mM KCl) containing a 1/5000 dilution of rabbit polyclonal anti-human serum albumin antibody (Boehringer Mannhein Biochemicals' 605 001). Plates are blocked the following morning for 3 h by the addition of 0.2 mL of PBS that contains 1% (w/v) bovine serum albumin (Sigma's A2153) to the wells containing the antibody solution. The wells are emptied and the plate is washed 5 times with PBS (made from 10× stock) by immersing the plate in PBS and shaking out the liquid.

Reaction mixtures are prepared in polypropylene microtiter plates (NUNC heat resistant, cat #442587) as follows. Library entities (0.002 mL in DMSO, 4 mM) are placed in the appropriate wells of the plates. The library consists of 100 member containing mixtures of the thiophenol esters and 5 members of the mixtures of the free acid forms of the biotinylated pentapeptides to give 105 total members of the library in each well. Each mixture is placed in six wells of the microtiter place, and subsequently 3 wells for a given mixture are either quenched by the addition of hydroxylamine at a final concentration of 50 mM in PBS or reacted with 0.01 mg/mL HSA in PBS. Positive controls consist of reacting HSA (0.01 mg/mL) with 0.08 mM NHS-biotin and background values are obtained by first reacting the same concentration of NHS-biotin with hydroxylamine and then adding enough HSA to the quenched mixture to give a final concentration of 0.01 mg/mL.

A stock solution of 10 mg/ml HSA (Sigma's A-8673) is prepared in PBS. A solution of HSA in PBS for the reaction with the library is prepared by adding 0.041 mL of 10 mg/ml HSA to 40 mL of PBS (0.010 mg/mL) and added to three wells of the six wells containing either library or NHS biotin (0.098 mL/well) to initiate the reaction at room temperature (21.4° C.). The reactions are terminated after 1 h by the addition of 0.005 mL of 1 M hydroxylamine, pH 7.7, and are allowed to react for >10 min before transferring to the corresponding 96 well plate that contains the polyclonal antibody required for capturing biotinylated HSA.

Reaction blanks are prepared by the addition of 0.098 mL of a solution of PBS/hydroxylamine, which was prepared by adding 2.04 mL of 1 M hydroxylamine, pH 7.7, to 38 mL PBS, to the library entities present in three wells of the polypropylene plate. These mixtures are allowed to stand for 10 min at room temperature before the addition of 0.005 mL of PBS containing 0.001 mg HSA, which is prepared by diluting 0.050 mL of the 10 mg/mL stock solution to 2.5 mL with PBS. This addition of HSA after reacting either the library or NHS biotin with hydroxylamine gives a final concentration of HSA in the quenched reaction mixtures of 0.010 mg/mL.

The majority of the contents (0.09 mL) of the reaction wells is transferred to the corresponding wells of the blocked plates, which contain 0.01 mL per well of the plate of 1% BSA and 0.5% Tween 20 in PBS. The plates are covered and let stand for 2 hours at room temperature to permit binding of HSA to the capture antibody. Following the time permitted for binding of HSA to antibody, the plates are washed 10 times with PBS as described above. A solution of PBS containing 0.1% Tween 20 (Sigma's P 1379, lot #15H0929) and a 500 fold dilution of each of Vector's A and B reagents (avidin-HRP conjugate) is prepared 0.5 h in advance of placing 0.1 mL of this solution in each well of the plates. The plates are incubated for 0.5 h at room temperature and then washed 10 times with PBS as described above. A solution (10 mL) of 0.111 M disodium phosphate, 0.044 M citric acid, pH 5.3, containing 5 mg OPD (Sigma's P 3804, lot

075H 8941) and 0.005 mL hydrogen peroxide (Sigma's H 1009, lot #75H3542) is prepared, and 0.1 mL of this is added to each well of the plates, and the plates are incubated for 0.5 h at room temperature in the light. The wells are acidified by the addition of 0.1 mL of 2 N sulfuric acid (VWR's VW3500 1, lot #9508266) and read at 490 nm in the endpoint mode of the plate reader.

Treatment of Data

Assays for the biotinylation of HSA by members of the library and by NHS biotin give triplicate values for both the biotinylation reaction and for the binding of quenched esters to the capture well. Average values and standard deviations (s.d.) of those average values of the triplicate measurement are calculated. A measure of the increase in absorbance that is dependent upon the labeling reaction of HSA by a member(s) of the library, and which is referred to as a sort value, is obtained by calculating a weighed fraction that describes the increase relative to the average value of the background mesurements for that member of the library. Equation 1 describes this fraction and is given below.

$$\text{sort value} = [\text{Avg. of Reaction OD} (2 \times \text{s.d.})]/[\text{Avg. of Background OD} + (2 \times \text{sd})]$$

Figure 2:
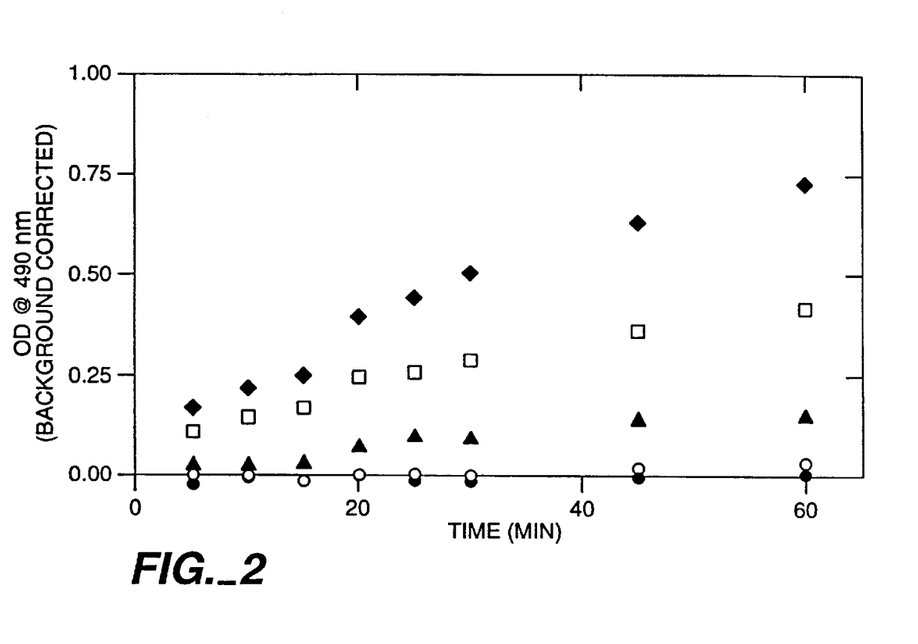
FIG. 2 is a graph of the rate of reaction of different peptide mixtures in comnparison to the rate of reaction of thiophenyl biotin, where the mixtures are described in Table 3.

Sort values greater than 1 represent biotinylation reactions that are significantly above background. The weighting of the fraction by either adding to the denominator or subtracting from the numerator the standard deviations of the average values biases the sort value to account for the uncertainty in the measured absorbances. Results: Table 2 gives the structures and sort values for the ten most reactive members of a pentameric amino acid affinity labeling library that contains biotin at the n terminus, an amide c termus and a thiophenyl ester function at the carboxyl group of glutamic acid (Glu*). Each member of the library consists of 100 labeling entities that differ in the order and composition of the amino acids present at positions 1 and 2.

nylation of HSA by these members of the library is shown in FIG. 2. The curves all show a characteristic early fast phase of reaction followed by a slowing of the reaction at later times. The maximal rate of reaction is determined by chosing the best straight line fit for the early values of the time course. Biotinylation of HSA by the thiophenyl ester of biotin was also measured, and the rate of this reaction is 0.002 OD units/min or less with a lower limit being 0.0004 OD units/min. FIG. 2 shows that the three reactive members of the library give both decreasing rates and extents of reaction in accordance with their decreasing sort values shown in Table 2.

Table 3 gives the observed increases in rate of reaction of the library members when compared to the thiophenyl ester of biotin. Members of the library differ in their structures from that of the thiophenyl ester of biotin in that a pentapeptide with a C- terminus amide is present and the ester function is spatially distinct because its position is on the amino acid side chain of glutamate. Table 3 shows that these differences in structure can account for rate increases between 4 and 65 fold over the thiophenyl ester of biotin alone.

TABLE III

| Ester | Rate (OD units/min) | Fold Increase over 80 µM thiophenyl biotin |
| --- | --- | --- |
| biotin-Glu-Arg-Trp-$X_2$-$X_1$-$NH_2$ | 0.026 | 13–65 |
| biotin-Glu-Trp-Arg-$X_2$-$X_1$-$NH_2$ | 0.015 | 8–38 |
| biotin-Glu-Arg-Leu-$X_2$-$X_1$-$NH_2$ | 0.007 | 4–18 |
| biotin-Glu-Arg-His-$X_2$-$X_1$-$NH_2$ | not observable | 0 |
| 80 mM Thiophenyl Biotin | 0.0004–0.002 | 1 |

It is evident from the above results that the subject method provides for an efficient and rapid method for identifying oligomeric sequences which have high affinity for a particu-

TABLE II

| Sort Order | Library Member | Sort Value | Change in Optical Density (background corrected) |
| --- | --- | --- | --- |
| 1 | biotin-Glu*-Arg-Tyr-$X_1$-$X_2$-$NH_2$ | 2.77 | 0.349 |
| 2 | biotin-Glu*-Trp-Arg-$X_1$-$X_2$-$NH_2$ | 2.41 | 0.385 |
| 3 | biotin-Glu*-Arg-Trp-$X_1$-$X_2$-$NH_2$ | 2.03 | 0.332 |
| 4 | biotin-Glu*-Leu-Arg-$X_1$-$X_2$-$NH_2$ | 1.88 | 0.296 |
| 5 | biotin-Glu*-Arg-Leu-$X_1$-$X_2$-$NH_2$ | 1.81 | 0.285 |
| 6 | biotin-Glu*-Tyr-Trp-$X_1$-$X_2$-$NH_2$ | 1.76 | 0.272 |
| 7 | biotin-Glu*-Tyr-Tyr-$X_1$-$X_2$-$NH_2$ | 1.72 | 0.264 |
| 8 | biotin-Glu*-Try-Glu-$X_1$-$X_2$-$NH_2$ | 1.66 | 0.254 |
| 9 | biotin-Glu*-Arg-Met-$X_1$-$X_2$-$NH_2$ | 1.63 | 0.217 |
| 10 | biotin-Glu*-Ser-Tyr-$X_1$-$X_2$-$NH_2$ | 1.57 | 0.181 |
| 71 | biotin-Glu*-Leu-Glu-$X_1$-$X_2$-$NH_2$ | 0.88 | 0.002 |
| Free Acid 1 | biotin-Glu-Leu-Tyr-$X_1$-$X_2$-$NH_2$ | 0.78 | 0.027 |
| Free Acid 2 | biotin-Glu-Leu-Met-$X_1$-$X_2$-$NH_2$ | 0.76 | 0.014 |
| Free Acid 3 | biotin-Glu-Trp-Glu-$X_1$-$X_2$-$NH_2$ | 0.70 | −0.019 |
| Free Acid 4 | biotin-Glu-Leu-Ser-$X_1$-$X_2$-$NH_2$ | 0.65 | 0.020 |
| Free Acid 5 | biotin-Glu-Leu-Leu-$X_1$-$X_2$-$NH_2$ | 0.64 | −0.025 |

Forty-one members of the library gave sort values greater than 1 while 32 members give values greater than 1.1 and 19 members give values greater than 1.2. The free acid forms of the library give sort values between 0.88 and 0.64. The changes in optical density are proportional to the extent of biotinylation of HSA, and the range of changes of optical density given in Table 2 demonstrates that individual members of the library react with HSA to different extents.

The rates of reaction of four members of the library with HSA were determined, and the kinetics describing the biotilar conformation of a protein, even in a mixture of proteins. Thus oligomers can be prepared which can be used in conjunction with physiologically active compounds for preferentially directing the physiologically active compounds to a protein target. The subject methods provide particular application to direct drugs to vascular associated proteins to enhance the lifetime of the drugs or provide for an alternative distribution of the drugs in the vascular system.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for selecting at least one member of a combinatorial library which preferentially binds to a target protein present in serum, cerebral spinal fluid or blood, wherein said target protein has a reactive functionality and said member of said library includes:
   (a) an oligomeric group;
   (b) a reactive functional group joined to said oligomeric group, wherein said reactive functional group is capable of forming a covalent bond with said reactive functionality on said target protein when said member of said library binds to said target protein and
   (c) a detectable labeling group, joined to said oligomeric group, wherein said detectable labeling group comprises a leaving group and said detectable labeling group is liberated upon formation of said covalent bond of step (b); the method comprising the steps of:
   i) activating the reactive functional group of each library member to form activated functional groups;
   ii) reacting said activated functional groups with each other in the absence of said target protein in a control reaction and reacting said activated functional groups and one or more target proteins in a target protein reaction; and
   iii) detecting the formation of a covalent bond between an activated functional group and a reactive functionality on said target protein by
      a) stopping said reaction at selected times in said control reaction and said target protein reaction;
      b) detecting the concentration of said labeling group in said target protein reaction at said selected times wherein the concentration of said detectable labeling group is proportional to the amount of detectable labeling group liberated upon formation of said covalent bond when said member of said library binds to said target protein and the amount, if any, of detectable labeling group released spontaneously by said library;
      c) detecting the concentration of said labeling group in said control reaction at said selected times wherein the concentration of said detectable labeling group in said control reaction is proportional to the amount, if any, of detectable labeling group released spontaneously by said library; and
      d) subtracting the concentration of detectable labeling group, if any, detected in step iii) c) from the concentration of detectable labeling group detected in step iii) b) to identify a target protein reaction which has a higher labeling group concentration than the labeling group concentration in said control reaction thereby allowing selection of at least one member of the combinatorial library which preferentially binds to the target protein.

2. The method of claim 1 wherein said leaving group is a nitrophenolate anion or a thiophenolate anion.

3. The method of claim 1 wherein said activated functional group is a carboxy group or a phosphoryl group.

4. The method of claim 3 wherein said activated functional group is a carboxy group.

5. The method of claim 4 wherein said carboxy group is activated with a chemical selected from the group consisting of carbodiimides, phenols, thiophenols, benzyl alcohols, N-hydroxy imides, phosphates and coumarins.

6. The method of claim 1 wherein said detectable labeling group is biotin.

7. The method of claim 1 wherein said serum, cerebral spinal fluid, or blood is human serum, cerebral spinal fluid or blood.

8. The method of claim 1 wherein the oligomeric group has an amino terminus and said reactive functional group is proximal to said amino terminus.

9. The method of claim 1 wherein the oligomeric group has a carboxyl terminus and the reactive functional group is proximal to said carboxyl terminus.

* * * * *